US00PP08924P

United States Patent [19]

Hesse

[11] Patent Number: Plant 8,924

[45] Date of Patent: Oct. 4, 1994

[54] CHRYSANTHEMUM PLANT NAMED SUNSET LADY

[75] Inventor: Peter S. Hesse, Nipomo, Calif.

[73] Assignee: Cleangro, Ltd., Wellington, England

[21] Appl. No.: 35,241

[22] Filed: Mar. 22, 1993

[51] Int. Cl.[5] ..... A01H 5/00
[52] U.S. Cl. ..... Plt./78
[58] Field of Search ..... Plt. 78, 76

*Primary Examiner*—Howard J. Locker
*Attorney, Agent, or Firm*—Arnold, White & Durkee

[57] ABSTRACT

The present invention comprises a new and distinct cultivar of Chrysanthemum, botanically known as *Dendranthema grandiflora,* and referred to by the cultivar name Sunset Lady. The new cultivar is distinguished by its red bronze buds and pale yellow flowers with a distinctive red color eye.

1 Drawing Sheet

BACKGROUND OF THE NEW PLANT

Sunset Lady, identified originally as No. 1 yellow sport of Wain's Pink Lady and thereafter coded as HM-1, was a spontaneous mutation (sport) discovered by Peter S. Hesse in a controlled breeding program during March, 1991 in Nipomo, Calif., USA. The striking red bronze bud color and the pale yellow fully expanded florets were unusual characteristics that appeared to make it a desirable plant for greenhouse production.

The first act of asexual reproduction of Sunset Lady was accomplished in June 1991 when vegetative cuttings were taken in a controlled environment in Nipomo, Calif. by technicians working under Peter S. Hesse.

Horticultural examination of controlled flowerings of successive plantings has shown that the unique combination of characteristics as herein disclosed for Sunset Lady are firmly fixed and are retained through successive generations of asexual reproduction.

Sunset Lady has not been observed under all possible environmental conditions. The phenotype may vary significantly with variations in the environment such as temperature, light intensity and day length.

The following observations, measurements and comparisons describe plants grown in controlled environments in Nipomo, Calif. Unrooted cuttings were directly stuck into 6.5 inch pots and grown under the natural temperature and day length prevailing in June 1991–December 1992.

The following traits have been repeatedly observed and are determined to be basic characteristics of Sunset Lady, which in combination distinguish this Chrysanthemum as a new and distinct cultivar.

1. Flat capitulum form.
2. Pale yellow color of fully expanded outer ray floret.
3. Red-bronze bud color contrasting with the pale yellow florets. This redness is always deeper in the center of the flower and radiates outward. This gives the flower a contrasting red colored "eye" during the stage before the ray florets are fully expanded. When fully expanded, the overall color is pale yellow with a somewhat deeper yellow appearance toward the center.
4. An average of 8.6 flowers/buds per break.
5. Diameter across the face of capitulum of 7.6 cm.

6. Exceptional upright spreading habit with an average of 4.0 breaks after a single pinch.
7. Relative ease in controlling plant height such that the finished height will range from 10 inches to 17 inches depending on pot size and market requirements.

DESCRIPTION OF THE PHOTOGRAPH

The accompanying photograph shows typical inflorescence and leaf characteristics of Sunset Lady, with the colors being as nearly true as possible with illustrations of this type. The photograph shows Sunset Lady grown as a pinched spray pot mum with 3 cuttings in a 6.5 inch pot.

DESCRIPTION OF THE PLANT

Of the commercial cultivars known to the inventor, the most similar in form, color, and habit to Sunset Lady is the cultivar identified as Wain's Pink Lady (U.S. Plant Pat. No. 8,573). Reference is made to Table I which compares certain characteristics of Sunset Lady with Wain's Pink Lady.

TABLE I

| CHARACTERISTIC | SUNSET LADY | WAIN'S PINK LADY |
|---|---|---|
| CAPITULUM FORMS | FLAT | FLAT |
| CAPITULUM TYPE | DECORATIVE | DECORATIVE |
| DIAMETER ACROSS FACE OF CAPITULUM | 7.6 CM | 7.7 CM |
| BRANCHING PATTERN | UPRIGHT SPREADING | UPRIGHT SPREADING |
| BREAKS/PINCH | 4.0 | 3.6 |
| HEIGHT IN 6.5 POT | 16–17 INCHES | 16–17 INCHES |
| RAY FLORET COLOR: | | |
| FRONT FULLY EXPANDED | 16C | 62D |
| FRONT UNFOLDED | 42C | 62A |
| FRONT BUD STAGE | 42C | 63D |
| BACK FULLY EXPANDED | 16C | 62B |
| BACK BUD STAGE | 42C | 63C |
| # RAY FLORETS | 172 | 152 |
| SHAPE OF RAY FLORETS | ELLIPTIC | ELLIPTIC |
| LENGTH OF RAY FLORETS | 3.6 CM | 3.7 CM |
| WIDTH OF RAY FLORETS | 1.1 CM | 1.22 CM |
| # OF FLOWERS/BREAK | 8.6 | 8.6 |
| LEAF COLOR | FRONT: 147 A BACK: 147 B | FRONT: 147 A BACK: 147 B |
| MATURE LEAF | 9.5 CM | 9.5 CM |

TABLE I-continued

| CHARACTERISTIC | SUNSET LADY | WAIN'S PINK LADY |
|---|---|---|
| LENGTH | | |
| MATURE LEAF | 5.7 CM | 5.7 CM |
| WIDTH | | |
| RESPONSE/TREATMENT | WEEKS TO FLOWERING: MEDIUM VIGOROUS GROWER | WEEKS TO FLOWERING: MEDIUM VIGOROUS GROWER |

Sunset Lady is similar to Wain's Pink Lady in growth habit and form, but has a distinctly different color. While Wain's Pink Lady is overall pink, Sunset Lady is a distinctive pale yellow with red eye. Buds on Sunset Lady are red/bronze.

The following lists the characteristic traits of the new cultivar Sunset Lady. Color designations are compared to the 1986 edition of R.H.S. Colour Chart, first published in 1966 by The Royal Horticultural Society, London, England. The B-Nine TM growth regulator referred to in the culturing procedures is 2,2-dimethyl hydrazide sold under the name of Alar or Daminozide and manufactured by UniRoyal.

Classification:

*Botanical.*—*Dendranthema grandiflora* cv. name Sunset Lady.

*Commercial.*—First decorative to be grown primarily as a 4.5–6.5 central bud removal (CBR) mum.

INFLORESCENCE

A. Capitulum:

*Form.*—Flat.

*Type.*—Decorative.

*Diameter across face.*—7.6 cm.

B. Corolla of ray florets:

*Color (general tonality from a distance of three meters).*—Pale yellow with a red center. Front: Fully expanded outer ray floret: 16C. Unfolded ray florets in center of flower: 42C. Back: Fully expanded outer ray floret: 16C. Front bud stage: Unexpanded outer ray floret: 42C. Back bud stage: Unexpanded outer ray floret: 42C.

*Shape.*—Elliptic.

C. Productive organs:

*Androecium.*—Not present.

*Gynoecium.*—Present in ray florets.

PLANT

A. General appearance:

*Height.*—When grown in a 6.5" pot with 1–3 applications of B-NINE TM (UniRoyal) at the rate of 2500 ppm, the total plant height from the bottom of the pot may be maintained at 16–18 inches. When grown in a 4.5" pot with 1–5 applications of B-NINE TM at the rate of 2500 ppm, the total plant height from the bottom of the pot may be maintained at 10–12 inches.

*Branching pattern.*—Upright and spreading with an average of 4.0 breaks when grown with one pinch as a spray pot.

B. Foliage:

*Color (upper surface).*—147 A.

*Color (lower surface).*—147 B.

*Shape.*—Typically five-lobed with relatively deep indentations between lobes giving the leaf a somewhat narrow appearance with an overall width of about 5.7 cm and an average length of about 9.5 cm (see photograph).

What is claimed is:

1. A new and distinct Chrysanthemum plant, substantially as herein described and shown, characterized by its red-bronze bud color and pale yellow flower with a reddish-bronze center in the mature expanded flower.

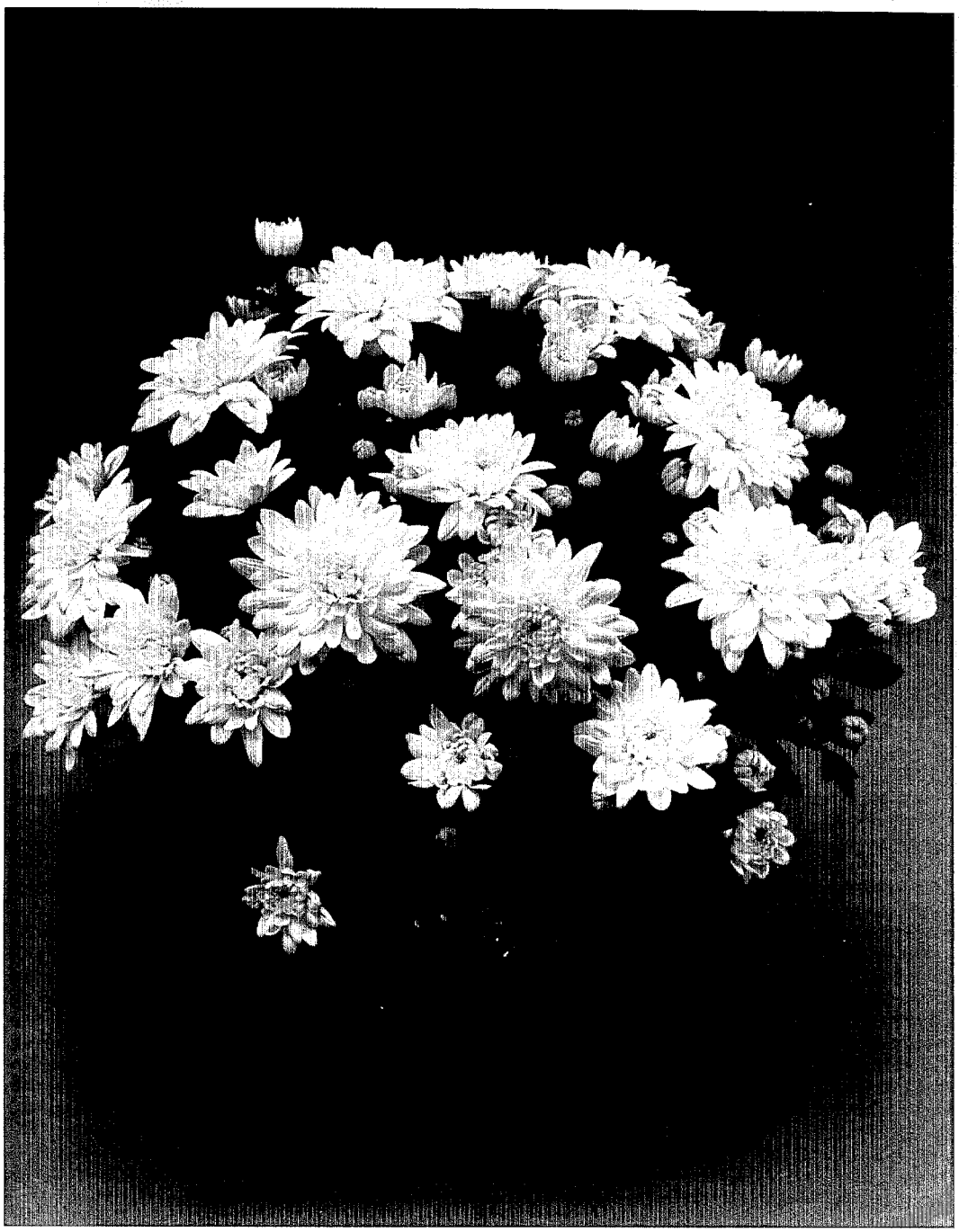

* * * * *